(12) United States Patent
Taylor

(10) Patent No.: US 6,190,342 B1
(45) Date of Patent: Feb. 20, 2001

(54) TAYLOR HARNESS

(76) Inventor: Earl J. Taylor, 1105 Dug Hill Rd., Mountain City, TN (US) 37683

( * ) Notice: Under 35 U.S.C. 154(b), the term of this patent shall be extended for 0 days.

(21) Appl. No.: 09/018,161

(22) Filed: Feb. 3, 1998

(51) Int. Cl.[7] .................................................. A61F 5/00
(52) U.S. Cl. ............................................................ 602/19
(58) Field of Search ............................ 602/19; 2/44, 45

(56) References Cited

U.S. PATENT DOCUMENTS

| | | | |
|---|---|---|---|
| 369,803 | * 9/1887 | McComber | 602/19 |
| 507,172 | * 10/1893 | Sheldon | 602/19 |
| 766,863 | * 8/1904 | Adams | 602/19 |

* cited by examiner

Primary Examiner—Kim M. Lewis
(74) Attorney, Agent, or Firm—Adrian J. Good; Susan F. Johnston

(57) ABSTRACT

A harness for the alleviation of back strain has members passing over the shoulders and around the thoraric region with attachments to a pivotable tension equalizing plate whereby the lumbar or lower back region is supported and a balance between the anterior and posterior muscle groups is attained.

13 Claims, 4 Drawing Sheets

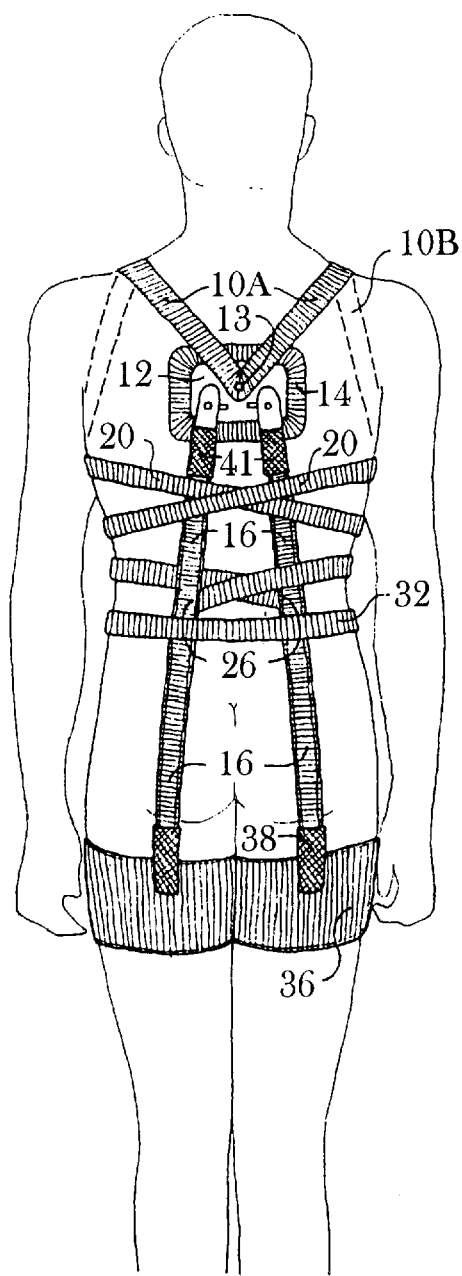
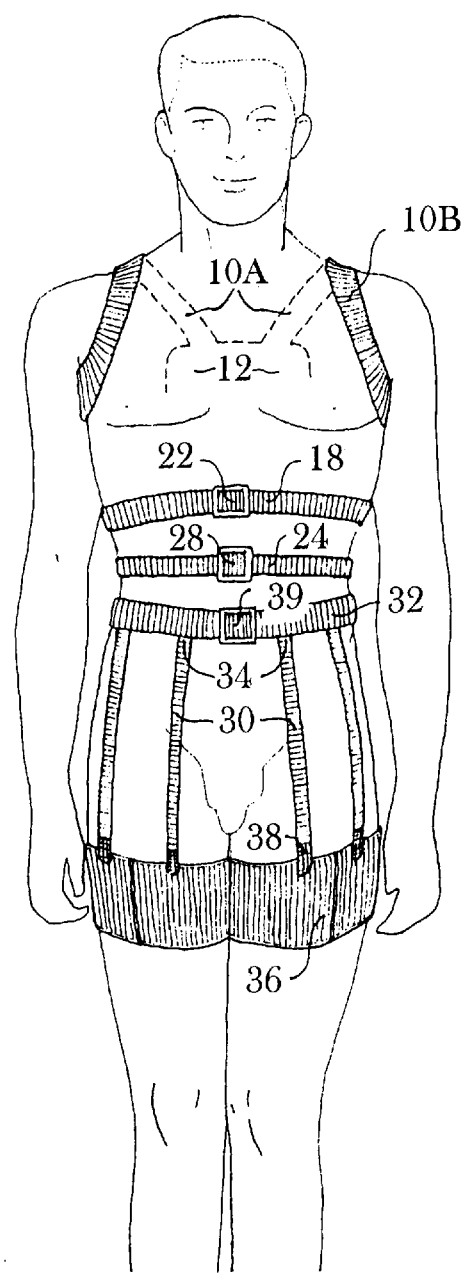
Fig. 1A
Fig. 1B

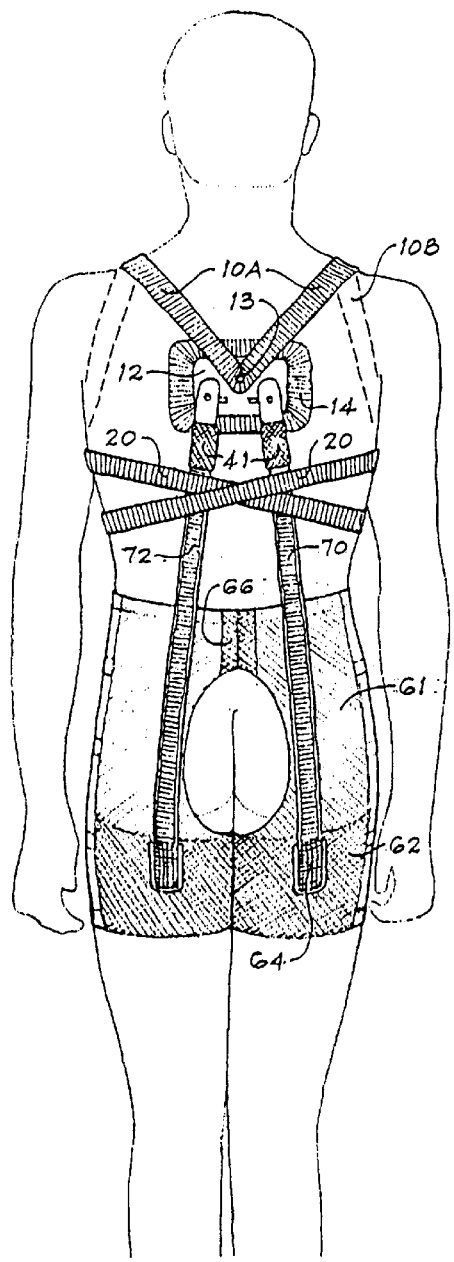
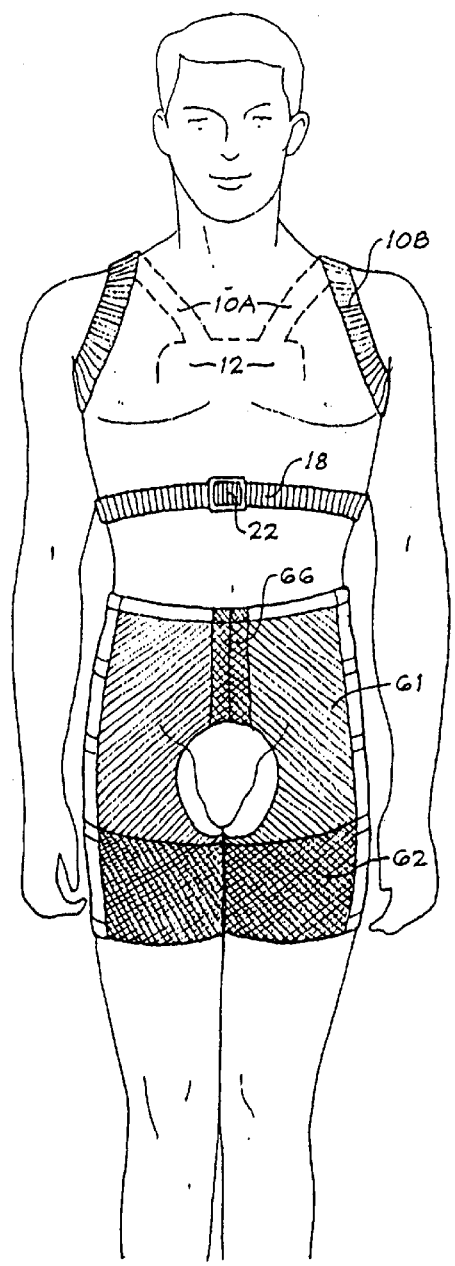
FIG. 3A
FIG. 3B

TAYLOR HARNESS

BACKGROUND OF THE INVENTION

When our distant ancestors, whether homo erectus or homo habilis, came out of the trees and stood upright, some portions of descendant homo sapiens anatomy remained specifically vulnerable to insults associated with an erect posture and its necessary variations. A particular portion of anatomy vulnerable to the insults caused by stresses of physical exertion is the lumbar or lower back region. Leaning over from the erect position and lifting from the flexed position results in an unbalance in tone of the anterior and posterior muscle groups. The measured distance, between a point at the top of the shoulders and a point below the buttocks or gluteus, is three to ten inches longer in the bent over or hip-flexed position than when the person is standing erect, depending on the height, weight and muscular configuration of the particular individual.

The stress of this extension and the resulting strain on the muscles, ligaments and vertebrae of the spine is a cause of much pain and disability to many people in all segments of society, from farmers tilling the soil to secretaries filing documents, to athletes, librarians, and especially to manual laborers.

Prior efforts in this field include: U.S. Pat. No. 4,629,183, Perrine, disclosing an arm support device with a body member and pivotable arm supports; U.S. Pat. No. 4,802,667, Altner, a weight lifter's belt for the abdomen; U.S. Pat. No. 5,147,261, Smith et al, a lifting belt, comprising lumbar and abdominal belts; U.S. Pat. No. 5,158,520, Lemke et al., a training device comprising a belt on the subject attached to a weight lifting apparatus, U.S. Pat. No. 5,212,380, Steinbrueck, disclosing an orthopedic back harness suspended from an elevated support; U.S. Pat. No. 5,406,942, Loo, disclosing a harness with a belt, a suspender, a cross-support and an ischial pocket; and U.S. Pat. No. 5,472,398, Silverman, disclosing a harness for exercises having rigid shoulder yokes for holding weights during squat exercises.

OBJECT OF THE INVENTION

The object of this invention is the provision of an apparatus designed to ease the strain on the thoraco-lumbar-pelvic region of the anatomy and to correct the imbalance in muscle tone in this region that occurs because greater muscular exertion is required assuming an erect position from hip-flexed position than from assuming an erect position to hip-flexed position. The harness of my invention has two purposes: (1) to strengthen and retone the anterior abdominal, sublumbar, thoracic and pelvic muscle groups, (2) to serve as an aid in lifting heavy objects from any hip-flexed position to the standing position. These objectives are accomplished simultaneously with my invention.

SUMMARY OF THE INVENTION

The Taylor Harness is an elastic harness having a shoulder harness, a tension equalizing plate, elastic back bands, leg straps and thigh bands, all interconnected in order to strengthen and support the abdominal and anterior sublumbar, thoracic and pelvic muscle groups.

DETAILED DESCRIPTION OF THE INVENTION

The purposes of the Taylor Harness are: (1) to strengthen the abdominal and anterior sublumbar thoracic and pelvic muscle groups and (2) to serve as an aid in lifting heavy material objects from any hip-flexed position to the standing position. Both purposes may be accomplished simultaneously.

The Taylor Harness consists of six continuous but separating component parts. These are (1) padded shoulder harness with Velcro® snap latch buckles, (2) a fulcrum type tension equalizing plate, (3) elastic rubber back bands with covers, (4) leg straps having knee and ankle supports with Velcro® or snap latch buckles, (5) thigh leg bands with supports and belt, and (6) a crotchless long legged brief shorts with Velcro® or snap latch fasteners.

The functional application of the component parts of the Taylor Harness are used to accomplish the above stated purposes as follows: (1) The leg straps cross the shoe soles of the user in front of the heel of the shoe. They then extend upward on the medial and lateral aspects of each ankle, and up each leg to the gluteal area. At a point adjacent to each ankle these straps are stabilized with adjustable ankle straps with pads. At a point just above the ankle these leg straps have snaps and/or vertical slits in each through which passes another padded strap. This second padded strap circles the ankle and is fastened on the upper part of the front of the foot at shoe lace level with Velcro® or snap fasteners. This padded strap, as it circles the foot above the ankle prevents the vertical straps from developing slack as they pass under the shoe sole in front of the heel of the shoe.

The leg straps extend upward on the medial and lateral aspect of each leg. At a point just below and just above the knee of each leg they, have slits or snaps in each through which pass padded straps. These padded straps encircle the leg above and below the knee and are fastened with Velcro® or snaps on the anterolateral aspect of each leg.

From the knee the vertical leg straps extend upward to a point just below the gluteal bulge. At this point each of the two vertical straps on each leg is attached to the ventral portion of the elastic back bands with adjustable snap locks, Velcro®, or other fasteners.

An alternate ventral anchoring system to the leg strap system is the upper thigh system. These upper thigh bands consist of two bands four to eight inches wide that encircle each thigh two to three inches ventral to the crotch. These thigh bands are fastened on the anterolateral aspect of each thigh with Velcro® fasteners. These bands are each supported by two narrow belts, which extend upward from the anteromedial and posterolateral aspect of each upper thigh band to their attachments to a narrow Velcro® fastened waist belt. This waist belt and four descending belts prevent the upper thigh bands from slipping down the thighs. These upper thigh bands are used as posterior anchors for the elastic rubber back bands when it would not be practical to use the leg strap anchor system.

A second alternate ventral anchoring system to the leg strap system is the crotchless long-legged brief shorts sytem, henceforth ("CLLB"). Shorts are made of leather, nylon or any of a number of other materials. The shorts cover the waist down to the lower thigh area. They separate into a front and rear half along a separating and attachment line from top to bottom on both sides from the lateral waist, lateral hip and lateral thigh. They are fastened at these same separating lines with Velcro® or snap latch fasteners. These shorts are crotchless from the upper pubic area ventrally, posteriorly and then dorsally to a point above the split of the buttocks. These shorts serve as a ventral attaching point via Velcro® or snap latch fasteners of the CLLB for some users with certain dress limitations and or comfort variations.

The elastic or rubber back bands are dual and run parallel as they travel upward from their attachments to the vertical leg straps, crotchless long-legged brief shorts, or upper thigh bands ventral to the gluteal bulge. These elastic back bands are covered with soft leather, fabric or nylon slide boots that protect the user from friction between skin or clothing and the elastic back bands. The slide boots cover the entire length of the elastic back bands and are attached to the shoulder harness via elastic cuffs at the tension equalizing plate in the upper-posterior thoracic area just below the shoulder blades. The slide boots are attached ventrally, with elastic cuffs, to the vertical leg straps in the gluteal area. The slide boots have a strap attached to each of their medial slides in the area of the fourth or fifth lumbar vertebrae. These belly straps transverse laterally from their medial attachments to the slide boots, encircle the lower abdomen and are attached to each other with Velcro® or snaps in the anterior abdomen. These straps serve to either separate or pull together the elastic rubber back bands as they pass over the gluteal, lumbar and thoracic areas. When attached, the belly straps pull the elastic rubber back bands together for lifting and/or for exercising. With the belly straps unfastened, the elastic rubber back bands and their slide boots may be slipped off the gluteus and on to the lateral sides of the hips. In this lateral hip position the user can sit, bend, and put all parts of the Taylor Harness into position for use or make adjustments, without there being pressure on the elastic rubber back bands. The elastic rubber back bands are attached, ventral to the shoulder blades, in the upper posterior thoracic area to the tension equalizing plate.

The tension equalizing plate functions to equalize the tension on the elastic rubber back bands as the user walks, bends, or lifts.

The tension equalizing plate is an inverted triangular shape snapped apparatus with three points of attachment. The tension equalizing plate is attached to the shoulder harness at one of its points and to the top of each elastic rubber back band at its other two points. The tension equalizing plate (TEP) has a heavy friction pad underneath it on which it pivots. This pad is to prevent friction between the skin or clothing of the user as the TEP pivots as a fulcrum to equalize the tension of the elastic rubber back bands as the user walks. The TEP has slotted adjustment points at the attachment point of the elastic rubber back bands. These slotted adjustment points on the TEP allow for compensation in elastic rubber back band tension to be made for users of differing heights and strides as they walk.

The padded shoulder harness forms a "V" configuration on the back of the user in the area of the shoulder blades. It is at the ventral portion of this "V" configuration that the elastic rubber back bands are attached to the shoulder harness via the tension equalizing plate with Velcro® and adjustable snap buckles. The two top straps of the "V" pass over the shoulders between the neck and the scapulo-humeral joints upwardly and forwardly. They then pass ventrally and posteriorly under the arms over the lateral aspect of the rib cage, to the center of the back where they cross in the vicinity of the last thoracic vertebra. They pass under the elastic rubber back bands at their point of crossing and continue anteriorally around the rib cage and are attached in front near the ventral sternal area with Velcro® and or snap buckles.

The Taylor Harness accomplishes its stated purposes because it takes advantage of the fact that the anatomical measured distance between a point at the top of the shoulders and a point below the buttocks or gluteus is three to ten inches shorter in the standing position than it is when bent over or in the hip-flexed position, depending on the height and weight of the individual. The application of elastic bands, via a stable shoulder harness to a stable point at the bottom of the foot or upper thigh, makes it possible to store energy expended in bending the body at the sacrofemoral and vertebral joints. This energy thus stored in the elastic rubber bands is in turn utilized to assist the posterior thoracic, lumbar and pelvic muscles in the lifting process.

In essence what the Taylor Harness does is shift part of the workload of the lifting process from those posterior muscle groups of the shoulders, rib cage, spinal column, pelvis, and upper thighs, as we bend from the "pelvic extended" position and lift from the "pelvic flexed" position, to those anterior muscle groups of the thoracic cage, shoulders, the abdomen, the spinal column, pelvic and thigh.

By wearing the Taylor Harness "part time" the maintenance of a balance of muscle tone in all muscle groups mentioned is attained and maintained. A balance in muscle tone in the spinal musculature, especially in the lumbar area is essential if spinal nerve irration is to be alleviated or prevented. With the poor physical condition of most people today, the use of the Taylor Harness part time, would retone anterior muscle groups, that are seldom used, and as a result would aid in treating and greatly reduce the incidence of lumbrosacral disc syndrome.

These conditions are a result of an imbalance in muscle tone of the anterior and posterior muscle groups. This imbalance of muscle tone causes the rupture of the posterior side of the annulas fibrosa, a narrowing of the intervertebral space, thus the pinching of colateral nerves and spinal cord pressure.

The industrial applications, for workers bending and lifting, would be greatly reduced if workers were fitted with and wore the Taylor Harness part time on the job. The Taylor Harness would be invaluable in the treatment of those individuals already experiencing an episode of lumbar disc rupture.

Although Velcro® is described here, other fasteners, such as snaps, buttons, buckles and the like may also be used. The straps are principally nylon or leather, but other materials may be equally substituted. The TEP is normally reinforced fiberglass or metal but plastic or other material can also be used.

DESCRIPTION OF THE DRAWINGS

In FIGS. 1A and 1B with leg band anchor the shoulder harness 10 is shown back 10A and front 10B attached to the TEP 12 at 13 with flexible friction pad 14, and elastic back bands 16 with covers. Shoulder harness release belt 18 is a continuation at 20 of shoulder harness 10B and crosses the lateral rib cage to the posterior thoracic area where it crosses itself and proceed anteriorally around the abdominal wall and is fastened at 22. The elastic band release belt 24 is attached to back band slip covers at 26 and buckles at 28. Leg band supports 30 are for use with the thigh bands 38, are attached to a leg band support belt 32 at 34, leg band support belt buckles at 39, and are attached to thigh bands 36 at attachment points 38.

Figure 2A:
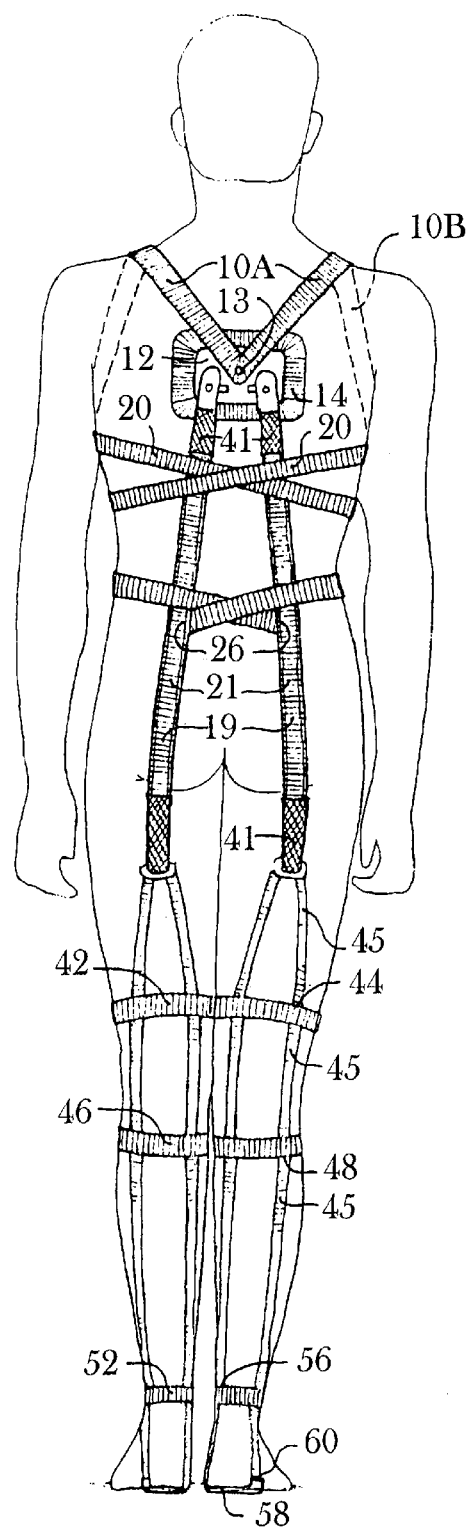
In FIGS. 2A and 2B with foot anchor shoulder harness 10A and 10B is attached to TEP 12 at 13 with friction pad 14, and elastic back bands of rubber or other elastomer 21 with leather, cloth, or knit covers, having elastic cuffs 41. Shoulder harness release belt 18 is a continuation of shoulder harness 10A and 10B at 20 held fastened at 22. Elastic band release belt 24 is fastened at 28 and attached to elastic back band cover 19 at 26. Elastic back bands 21 are attached to vertical leg bands 45 at 44 with fasteners 43. Lower knee straps 46 with fasteners 50 are attached to vertical leg straps 45 at 48.
Figure 2B:
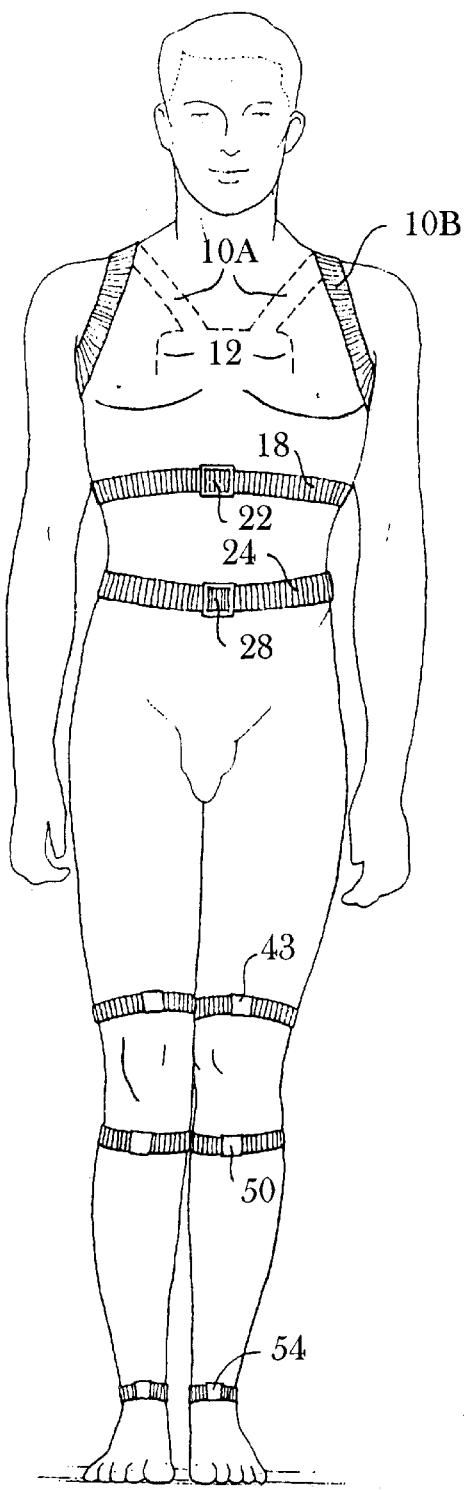

Upper knee straps 42 are attached to leg bands 45 at 44 and backed at fasteners 41. Ankle straps 52 with fasteners 54 are attached to elastic leg straps 45 at 56. Leg bands 45 are attached to foot anchor wear plate 58 at 60.

FIGS. 3A and 3B depict the upper thigh band system, the crotchless long legged brief comprising two bands 61 and 62 which encircle each thigh two to three inches ventral to the crotch. These thigh bands are fastened at 64 to belts 72 and 70 and fastened together at 66. Belts 72 and 70 are attached to TEP 12.

Figure 4:
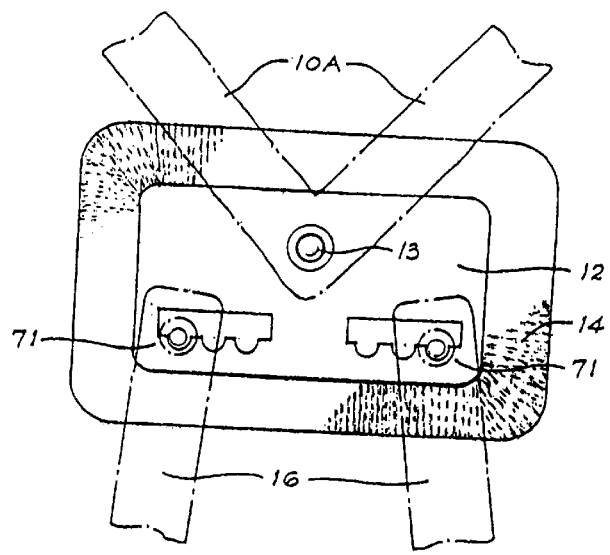

FIG. 4 shows a detail of TEP 12 with shoulder harness 10A attachment point 13, flexible friction pad 14 and elastic back bands 16 attached at 71.

Figure 5:
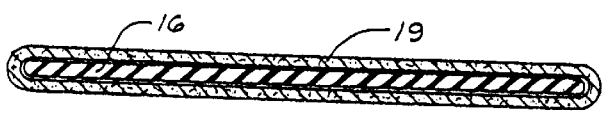

FIG. 5 is a cross-section of elastic back bands 16 with cover 19.

Figure 6:
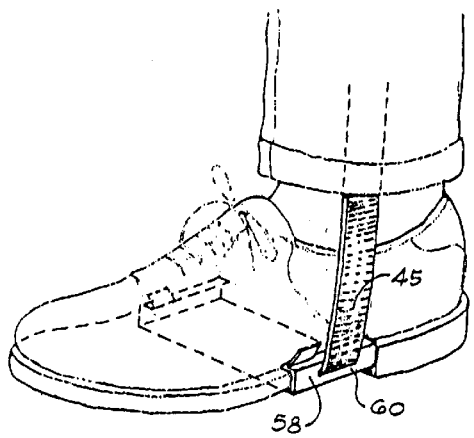

FIG. 6 depicts the foot anchor wear plate 58 fastened to vertical leg straps 45 at 60.

Figure 7:
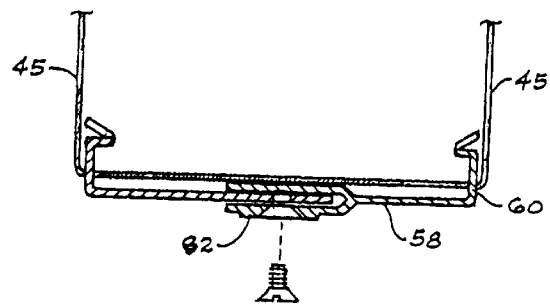

FIG. 7 depicts a cross-section of wear plate 58 with clamp 82 holding the two halves together and vertical leg straps 45.

I claim:

1. A harness adapted to strengthen the abdominal and anterior sublumbar muscle groups in homo sapiens, while simultaneously serving asan aid in lifting heavy objects from ahip-flexed to the standing position, said harness comprising:
    a) a tension equalizing plate having a fulcrum with a shoulder harness originating at said fulcrem with two members in a "V" configuration passing over the shoulders toa belt around the torso, said plate situated on the upper rear or posterior torso;
    b) said plate having a plurality of elastic back bands attached at a horizontal distance from said fulcrum;
    c) said back bands attached to vertical leg bands and to bands encircling the legs.

2. A harness adapted to strengthen the abdominal and anterior sublumbar muscle groups in a Homo sapien patient, while simultaneously serving as an aid in lifting heavy objects from a hip-flexed position to a standing position, said apparatus comprising:
    (a) a rigid tension equalizing plate having a fulcrum, said tension equalizing plate adapted to be positioned over an area of the patient's upper rear or posterior torso with said fulcrum covering the longitudinal center of the patient's body, said tension equalizing plate including a pair of attachment points disposed below said fulcrum defining a triangular configuration with said pair of attachment points being positioned on opposite sides of the longitudinal center;
    (b) two members attached to said fulcrum, said two members being adaptable to extend, in an essentially mirror image manner with each other, from said fulcrum over each respective shoulder to form a "V" configuration extending upwardly to opposite sides of the neck where each of said members further extends forwardly between the respective neck and the scapulo-humeral joints then ventrally and posteriorly below each respective armpit across the lateral aspect of the rib cage toward the center of the back where said members cross in the vicinity of the last thoracic vertebrae and further extend anteriorally around the rib cage to an anterior position near the ventral sternal area at which point said members are attachable to each other with a hook and loop fastening means or a fastening device;
    (c) a first pair of leg bands, each being adapted for being received around a different leg at a point between the gluteal area and the knee; and
    (d) a pair of elastic back bands, each of said pair of elastic back bands being adapted to attach to a different one of said pair of lower attachment points and attach to the corresponding leg band at a point so that each of said back bands extends between said corresponding lower attachment point and said first leg band at an angle and under an amount of tension sufficient to pull said attachment point inwardly downward toward the longitudinal center when the corresponding leg is extended forward, thus causing said tension equalizing plate to pivot around said fulcrum,
    whereby said harness provides a means for the patient to walk while being subjected to an increased tension between the knee area and the shoulder area.

3. The harness of claim 2 wherein said tension equalizing plate is mounted on a flexible friction pad sufficient to shield the patient from the pivoting action of said tension equalizing plate.

4. The harness of claim 2 wherein said elastic back bands are comprised of an elastomer and are covered with fabric covers.

5. The harness of claim 2 wherein each of said leg bands is adapted to be positioned around an upper thigh during use.

6. The harness of claim 2 further comprising a waist belt adapted to be received around the patient's waist, said waist belt having two oppositely positioned pairs of attaching straps extending therefrom, wherein each pair of attaching straps is adapted to attach to a different one of said pair of leg bands and provide support against downward slippage of the leg band.

7. The harness of claim 2 further comprising a second pair of leg bands adapted for being received around a different leg below the knees, and wherein said pair of elastic back bands extends to and connects to said second pair of leg bands.

8. The harness of claim 7 further comprising a third pair of leg bands adapted for being received around a different leg near the ankles, and wherein said pair of elastic back bands extends to and connects to said third pair of leg bands.

9. The harness of claim 2 further comprising a pair of wear plates adapted to lie under the soles of the feet at the instep, each of said pair of wear plates having a pair of leg straps extending upward therefrom from the medial and lateral aspects of each ankle to the gluteal area where each of said pair of leg straps for each said pair of wear plates is attached to said corresponding elastic back brace for the corresponding leg.

10. The harness of claim 9 wherein each of said pair of leg straps is attached to a corresponding leg band.

11. The harness of claim 2 further comprising crotchless pants, wherein said first pair of leg bands is an integral part of said crotchless pants.

12. The harness of claim 11 wherein said harness is adapted to alleviate the back strain of a large-breasted woman by supporting a portion of the weight of the breasts with said harness.

13. A harness adapted to strengthen the abdominal and anterior sublumbar muscle groups in a Homo sapien patient, while simultaneously serving as an aid in lifting heavy objects from a hip-flexed position to a standing position, said apparatus comprising:
    (a) a rigid tension equalizing plate having a fulcrum, said tension equalizing plate adapted to be positioned over an area of the patient's upper rear or posterior torso with said fulcrum covering the longitudinal center of the patient's body, said tension equalizing plate including a pair of attachment points disposed below said fulcrum defining a triangular configuration with said pair of attachment points being positioned on opposite sides of the longitudinal center, said tension equalizing plate being adapted to pivot at said fulcrum while positioned on the patient;

(b) two members pivotally attached to said fulcrum, said two members being adaptable to extend, in an essentially mirror image manner with each other, from said fulcrum over each respective shoulder to form a "V" configuration extending upwardly to opposite sides of the neck where each of said members further extends forwardly between the respective neck and the scapulo-humeral joints then ventrally and posteriorly below each respective armpit across the lateral aspect of the rib cage toward the center of the back where said members cross in the vicinity of the last thoracic vertebrae and further extend anteriorally around the rib cage to an anterior position near the ventral sternal area at which point said members are attachable to each other with a hook and loop fastening means or a fastening device;

(c) a pair of elastic back bands, each of said pair of elastic back bands being adapted to attach to a different one of said pair of lower attachment points and extend to the upper gluteal area when stretched (d) a first pair of leg bands, each being adapted for being received around a different leg at a point just above the knees, a second pair of leg bands adapted for being received around a different leg below the knees, and a third pair of leg bands adapted for being received around a different leg just above the ankles;

(e) a pair of leg straps, each of said pair of leg straps adapted to cross under the instep of the patient's foot and extending upward therefrom from the medial and lateral aspects of each ankle and up the posterior of the corresponding leg and attaching to said corresponding elastic back band, wherein each of said pair of leg straps is adapted to be fastenable to the corresponding third leg band at a point adjacent to each ankle with adjustable ankle strap with pads and fastenable to the corresponding first and second leg band at posterior point causing each of said elastic back bands to be extended from said corresponding lower attachment point at an angle and under an amount of tension sufficient to pull said attachment point inwardly downward toward the longitudinal center when the corresponding leg is extended forward, thus causing said tension equalizing plate to pivot in a pendulum fashion around said fulcrum, whereby said harness provides a means for the patient to walk while being subjected to an increased tension between the knee area and the shoulder area.

* * * * *

UNITED STATES PATENT AND TRADEMARK OFFICE
CERTIFICATE OF CORRECTION

PATENT NO. : 6,190,342 B1
DATED : February 20, 2001
INVENTOR(S) : Earl J. Taylor It is certified that error appears in the above-identified patent and that said Letters Patent is hereby corrected as shown below:

Column 5,
Claim 1 should be omitted

Signed and Sealed this

Twentieth Day of November, 2001

*Attest:*

*Attesting Officer*

NICHOLAS P. GODICI
*Acting Director of the United States Patent and Trademark Office*